(12) United States Patent
Cumming

(10) Patent No.: US 6,387,126 B1
(45) Date of Patent: *May 14, 2002

(54) ACCOMMODATING INTRAOCULAR LENS HAVING T-SHAPED HAPTICS

(76) Inventor: J. Stuart Cumming, 1211 W. LePalma Ave., #201 Anaheim, CA (US) 92801

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 08/858,978

(22) Filed: May 20, 1997

Related U.S. Application Data

(63) Continuation-in-part of application No. 08/388,735, filed on Feb. 15, 1995, now abandoned.

(51) Int. Cl.[7] ................................................. A61F 2/16
(52) U.S. Cl. ...................... 623/6.37; 623/6.39; 623/6.44
(58) Field of Search ............................. 623/6, FOR 105

(56) References Cited

U.S. PATENT DOCUMENTS

| | | | | |
|---|---|---|---|---|
| 4,174,543 A | * | 11/1979 | Kelman | 623/6 |
| 4,254,509 A | | 3/1981 | Tennant | |
| 4,254,510 A | * | 3/1981 | Tennant | 623/6 |
| 4,409,691 A | | 10/1983 | Levy | |
| 4,441,217 A | * | 4/1984 | Cozean | 623/6 |
| 4,477,931 A | | 10/1984 | Kelman | |
| 4,664,666 A | * | 5/1987 | Barrett | 623/6 |
| 4,673,406 A | * | 6/1987 | Schlegel | 623/6 |
| 4,704,123 A | | 11/1987 | Smith | |
| 4,718,904 A | | 1/1988 | Thornton | |
| 4,840,627 A | | 6/1989 | Blumenthal | |
| 4,880,427 A | * | 11/1989 | Anis | 623/6 |
| 4,936,850 A | | 6/1990 | Barrett | |
| 4,994,082 A | | 2/1991 | Richards et al. | |
| 5,078,742 A | | 1/1992 | Dahan | |
| 5,476,514 A | * | 12/1995 | Cumming | 623/6 |
| 5,522,891 A | * | 6/1996 | Klaas | 623/6 |

FOREIGN PATENT DOCUMENTS

| | | | | |
|---|---|---|---|---|
| GB | 2 171 912 A | * | 9/1986 | 623/6 |

OTHER PUBLICATIONS

D. Jackson Coleman, M.D., On The Hydraulic Suspension Theory of Accommodation, Tr. Am. Opth. Soc. vol. LXXXIV, 1986, pp. 846–868.

J. Stuart Cumming, M.D., Accomodating Intra–Ocular Lens Development & Clinical Results, Powerpoint presentation, 1999–2000. (14 pages).

Archimede Busacca, Ciliary Muscle Physiology Studied By Gonioscopy, Annals of Oculistics, vol. CLXXXVIII, Jan. 1955, (English Translation) (13 pages).

Archimede Busacca, La Physiologid Du Muscle Ciliaire Etudiee par la Gonioscopie, Annales D'Oculistique, Tome CLXXXVIII. 1$^{re}$ Livraison, Janvier 1955 (French Translation), pp. 1–21.

* cited by examiner

*Primary Examiner*—David H. Willse
(74) *Attorney, Agent, or Firm*—Fulbright & Jaworski L.L.P.

(57) ABSTRACT

An accommodating intraocular lens having anteriorly and posteriorly movable extended portions, such as T-shaped haptics, extending from a central optic to be implanted within a natural capsular beg of a human eye with the extended portions positioned between an anterior capsular rim and a posterior capsule of the bag, whereby during a post-operative healing period, fibrosis occurs about the extended portions to fixate the lens in the bag in a manner such that subsequent natural contraction and relaxation of the ciliary muscle moves the optic to provide vision accommodation of increased accommodation amplitude and diopters of accommodation.

52 Claims, 8 Drawing Sheets

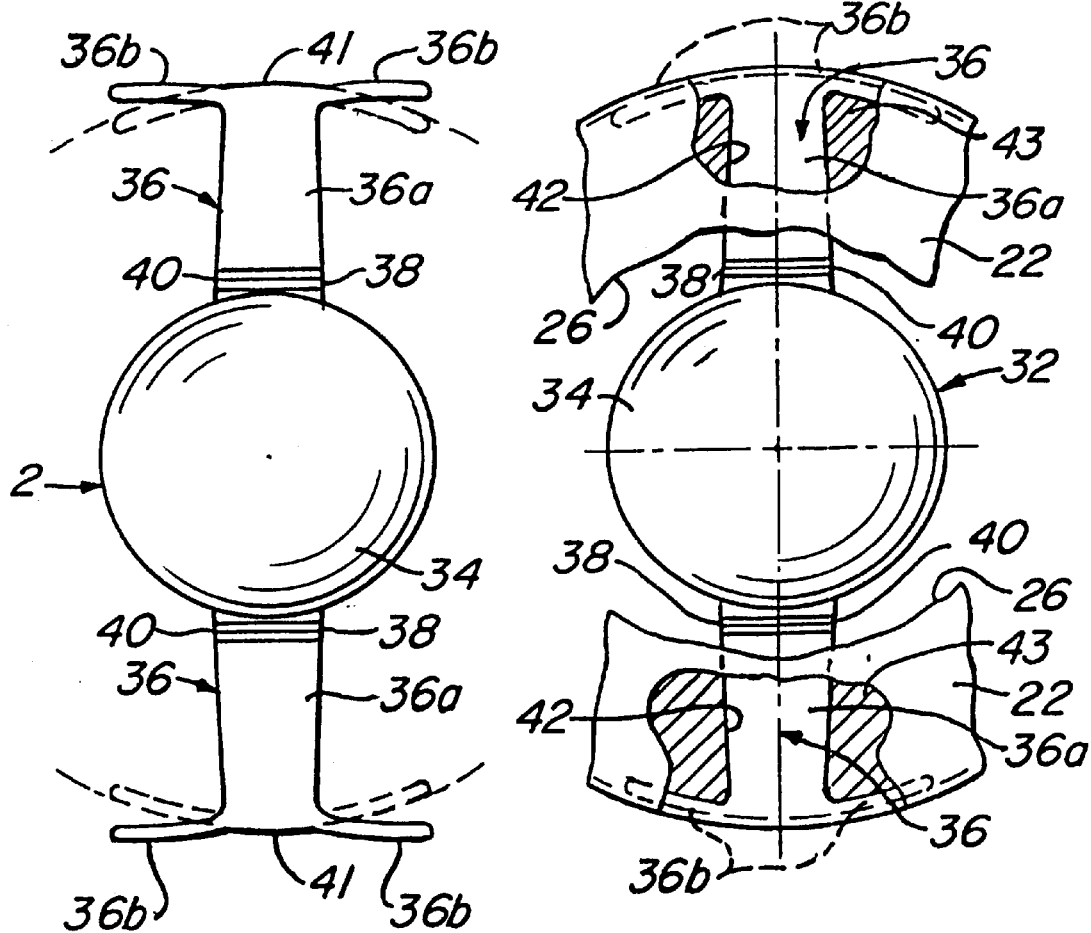
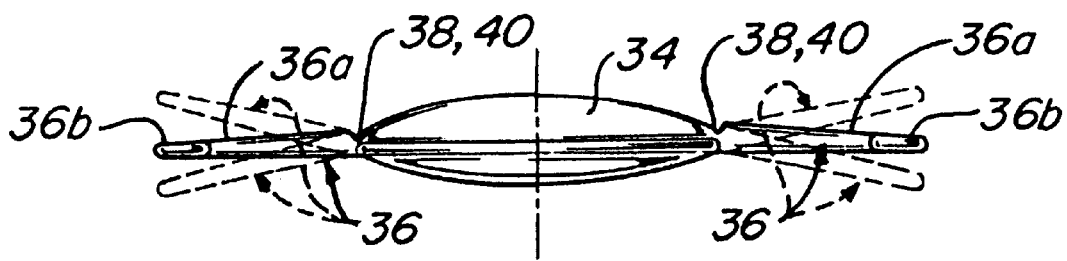

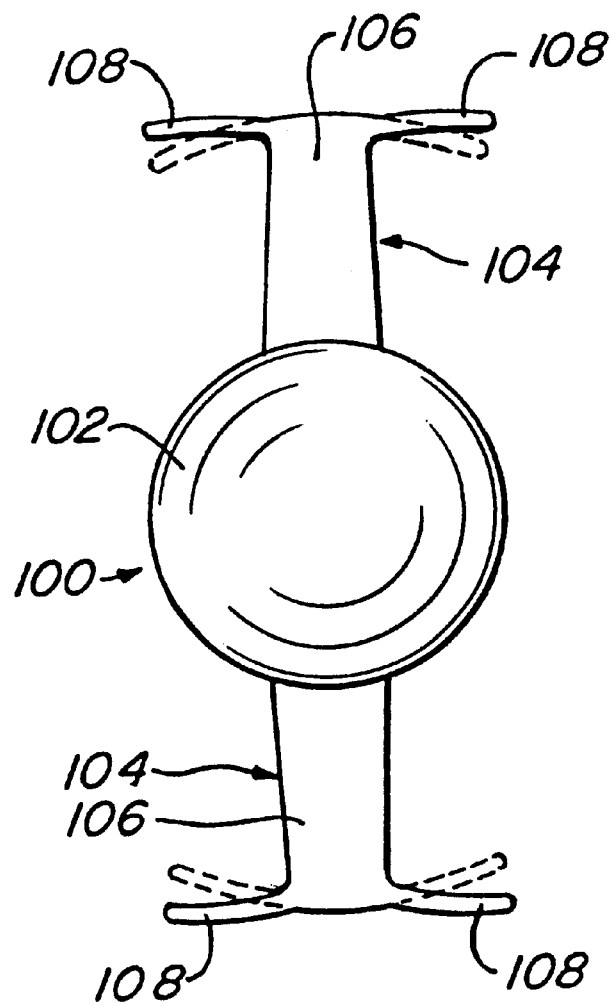
FIG.—9
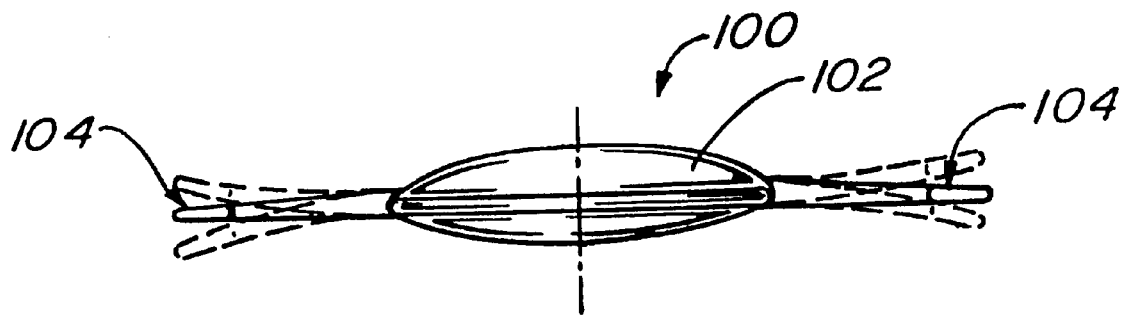
FIG.—10

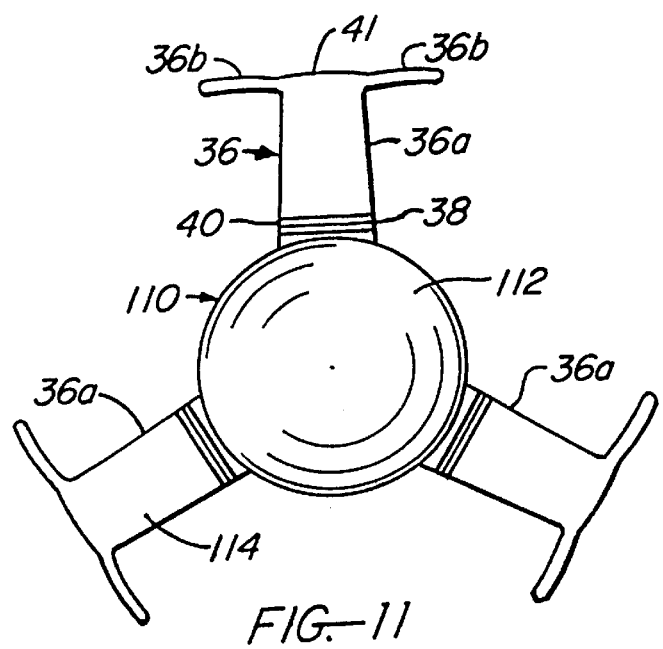
FIG.—11
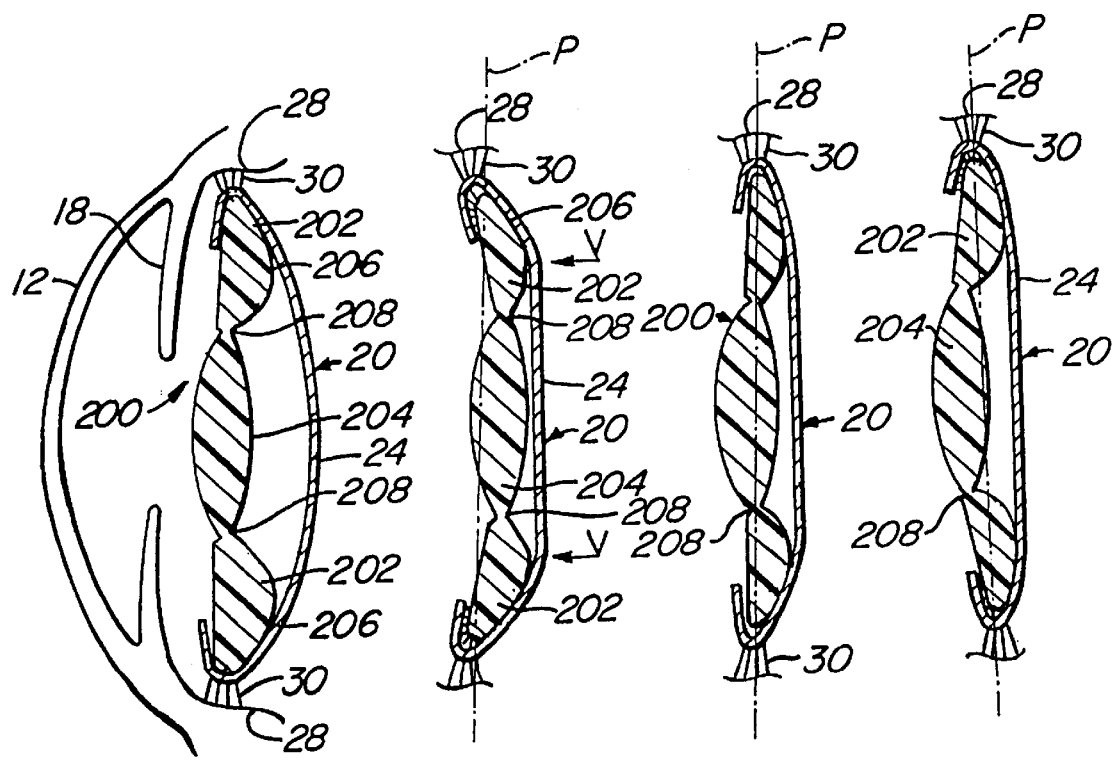
FIG.—12  FIG.—13  FIG.—14  FIG.—15

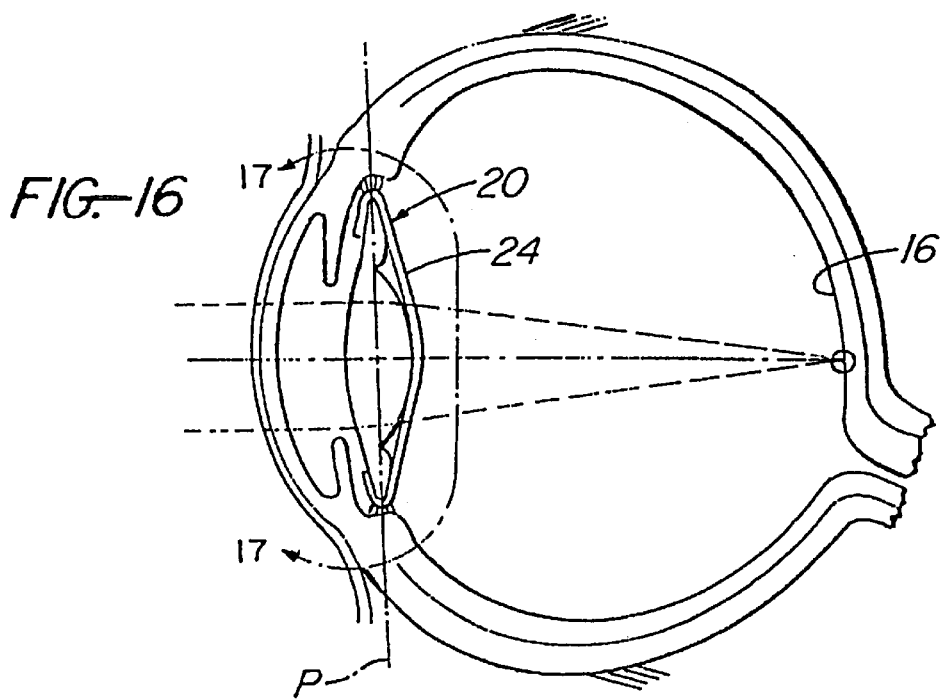
FIG.-16
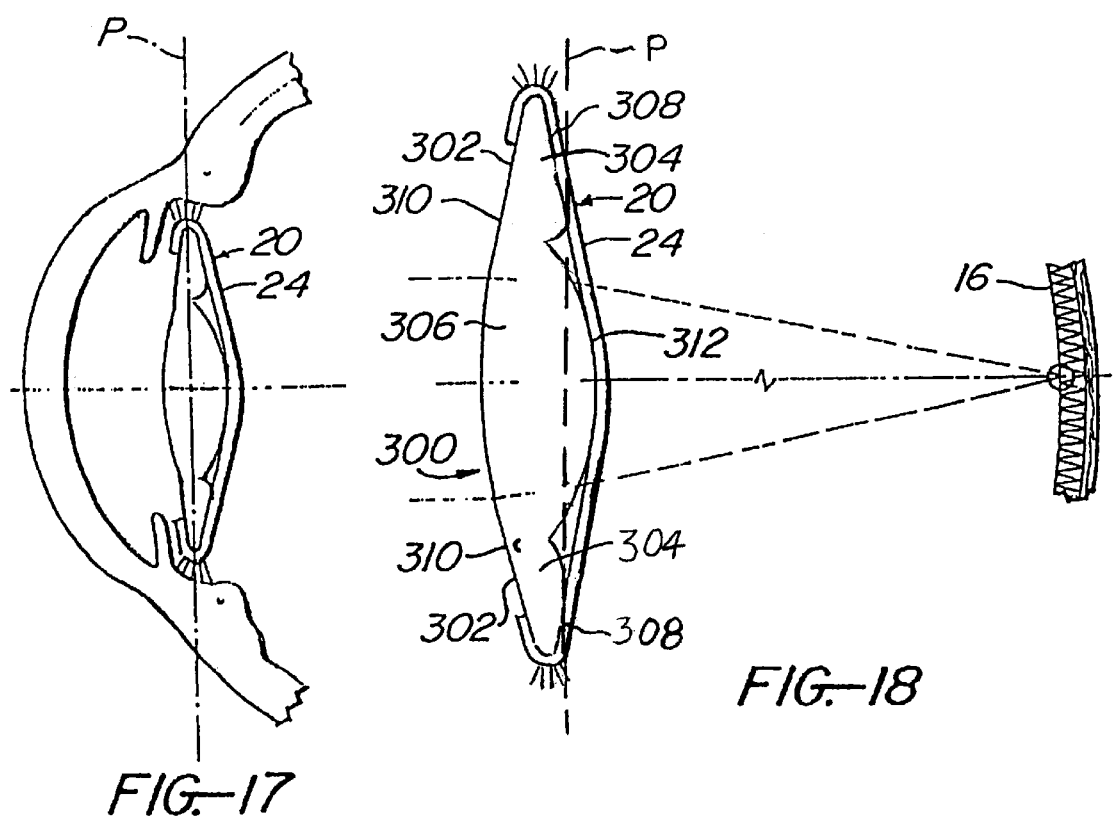
FIG.-17
FIG.-18

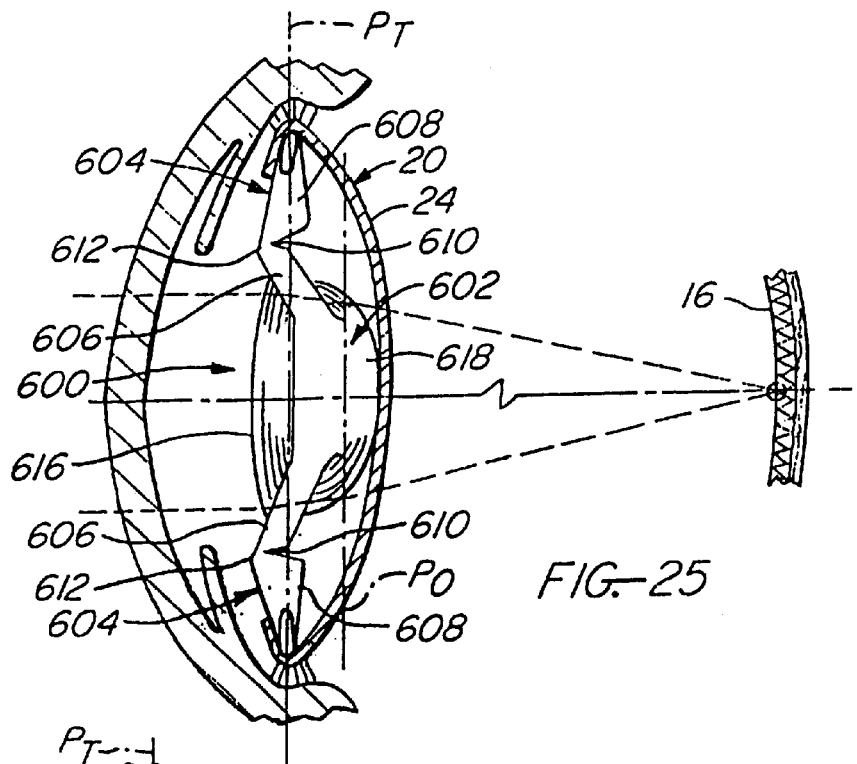
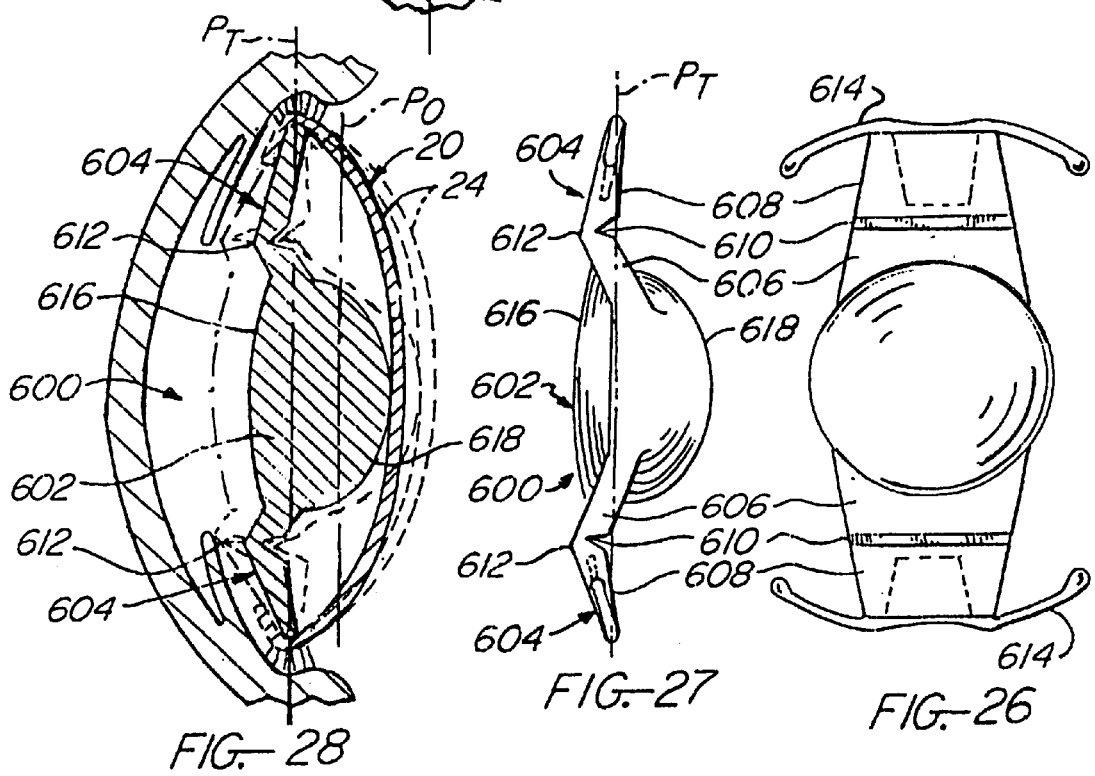
FIG.-25
FIG.-28
FIG.-27
FIG.-26

ACCOMMODATING INTRAOCULAR LENS HAVING T-SHAPED HAPTICS

RELATED APPLICATIONS

This application is a continuation-in-part of my application Ser. No. 08/388,735, filed Feb. 15, 1995, now abandoned.

Reference is made to my copending application Ser. No. 08/640,118, which is a continuation, with intermediate continuation applications of my U.S. Pat. No. 5,476,514. Reference is also made to my U.S. Pat. No. 5,496,366.

BACKGROUND OF THE INVENTION

This invention relates generally to intraocular lenses to be implanted within a natural capsular bag in the human eye formed by evacuation of the crystalline matrix from the natural lens of the eye through a anterior capsulotomy in the lens. The invention relates more particularly to novel accommodating intraocular lenses of this kind having a number of improved features including, most importantly, increased amplitude or diopters of accommodation.

The human eye has an anterior chamber between the cornea and iris, a posterior chamber behind the iris containing a crystalline lens, a vitreous chamber behind the lens containing vitreous humor, and a retina at the rear of the vitreous chamber. The crystalline lens of a normal human eye has a lens capsule attached about its periphery to the ciliary muscle of the eye by zonules and containing a crystalline lens matrix. This lens capsule has elastic optically clear anterior and posterior membrane-like walls commonly referred to by ophthalmologists as anterior and posterior capsules, respectively. Between the iris and the ciliary muscle is an annular crevice-like space called the ciliary sulcus.

The human eye possesses natural accommodation capability. Natural accommodation capability involves relaxation and contraction of the ciliary muscle of the eye by the brain to provide the eye with near and distant vision. This ciliary muscle action is automatic and shapes the natural crystalline lens to the appropriate optical configuration for focusing on the retina the light rays entering the eye from the scene being viewed.

The human eye is subject to a variety of disorders which degrade or totally destroy the ability of the eye to function properly. One of the more common of these disorders involves progressive clouding of the natural crystalline lens matrix resulting in the formation of what is referred to as a cataract. It is now common practice to cure a cataract by surgically removing the cataractous human crystalline lens and implanting an artificial intraocular lens in the eye to replace the natural lens. The prior art is replete with a vast assortment of intraocular lenses for this purpose.

Intraocular lenses differ widely in their physical appearance and arrangement. This invention is concerned with intraocular lenses of the kind having a central optical region or optic and haptics which extend outward from the optic and engage the interior of the eye in such a way as to support the optic on the axis of the eye.

Up until the late 1980s, cataracts were surgically removed by either intracapsular extraction involving removal of the entire human lens including both its outer lens capsule and its inner crystalline lens matrix, or by extracapsular extraction involving removal of the anterior capsule of the lens and the inner crystalline lens matrix but leaving intact the posterior capsule of the lens. Such intracapsular and extracapsular procedures are prone to certain post-operative complications which introduce undesirable risks into their utilization. Among the most serious of these complications are opacification of the posterior capsule following extracapsular lens extraction, intraocular lens decentration, cystoid macular edema, retinal detachment, and astigmatism.

An improved surgical procedure called anterior capsulotomy was developed to alleviate the above and other post-operative complications and risks involved in intracapsular and extracapsular cataract extraction. Simply stated, anterior capsulotomy involves forming an opening in the anterior capsule of the natural lens, leaving intact within the eye a capsular bag having an elastic posterior capsule, an anterior capsular remnant or rim about the anterior capsule opening, and an annular crevice, referred to herein as a cul-de-sac, between the anterior capsule remnant and the outer circumference of the posterior capsule. This capsular bag remains attached about its periphery to the surrounding ciliary muscle of the eye by the zonules of the eye. The cataractous natural lens matrix is extracted from the capsular bag through the anterior capsule opening by phacoemulsification and aspiration or in some other way after which an intraocular lens is implanted within the bag through the opening.

A relatively recent and improved form of anterior capsulotomy known as capsulorhexis is essentially a continuous tear circular or round capsulotomy. A capsulorhexis is performed by tearing the anterior capsule of the natural lens capsule along a generally circular tear line substantially coaxial with the lens axis and removing the generally circular portion of the anterior capsule surrounded by the tear line. A continuous tear circular capsulotomy or capsulorhexis, if performed properly provides a generally circular opening through the anterior capsule of the natural lens capsule substantially coaxial with the axis of the eye and surrounded circumferentially by a continuous annular remnant or rim of the anterior capsule having a relatively smooth and continuous inner edge bounding the opening. When performing a continuous tear circular capsulorhexis, however, the anterior rim may sometimes be accidentally torn, nicked, or otherwise ruptured, which renders the rim prone to tearing when the rim is stressed, as it is during fibrosis as discussed below.

Another anterior capsulotomy procedure, referred to as an envelope capsulotomy, involves cutting a horizontal incision in the anterior capsule of the natural lens capsule, then cutting two vertical incisions in the anterior capsule intersecting and rising from the horizontal incision, and finally tearing the anterior capsule along a tear line having an upper upwardly arching portion which starts at the upper extremity of the vertical incision and continues in a downward vertical portion parallel to the vertical incision which extends downwardly and then across the second vertical incision. This procedure produces a generally archway-shaped anterior capsule opening centered on the axis of the eye. The opening is bounded at its bottom by the horizontal incision, at one vertical side by the vertical incision, at its opposite vertical side by the second vertical incision of the anterior capsule, and at its upper side by the upper arching portion of the capsule tear. The vertical incision and the adjacent end of the horizontal incision form a flexible flap at one side of the opening. The vertical tear edge and the adjacent end of the horizontal incision form a second flap at the opposite side of the opening.

A third capsulotomy procedure, referred to as a beer can or can opener capsulotomy, involves piercing the anterior capsule of the natural lens at a multiplicity of positions along a circular line substantially coaxial with the axis of the eye and then removing the generally circular portion of the capsule circumferentially surrounded by the line. This procedure produces a generally circular anterior capsule opening substantially coaxial with the axis of the eye and bounded circumferentially by an annular remnant or rim of the anterior capsule. The inner edge of this rim has a multiplicity of scallops formed by the edges of the pierced holes in the anterior capsule which render the annular remnant or rim prone to tearing radially when the rim is stressed, as it is during fibrosis as discussed below.

Intraocular lenses also differ with respect to their accommodation capability and their placement in the eye. Accommodation is the ability of an intraocular lens to accommodate, that is, to focus the eye for near and distant vision. Certain patents describe alleged accommodating intraocular lenses. Other patents describe non-accommodating intraocular lenses. Most non-accommodating lenses have single focus optics which focus the eye at a certain fixed distance only and require the wearing of eye glasses to change the focus. Other non-accommodating lenses have bifocal optics which image both near and distant objects on the retina of the eye. The brain selects the appropriate image and suppresses the other image, so that a bifocal intraocular lens provides both near vision and distant vision sight without eyeglasses. Bifocal intraocular lenses, however, suffer from the disadvantage that each bifocal image represents only about 40% of the available light, and a remaining 20% of the light is lost in scatter.

There are four possible placements of an intraocular lens within the eye. These are (a) in the anterior chamber, (b) in the posterior chamber, (c) in the capsular bag, and (d) in the vitreous chamber. The intraocular lenses disclosed herein are for placement in the capsular bag.

SUMMARY OF THE INVENTION

This invention provides an improved accommodating intraocular lens to be implanted within a capsular bag of a human eye which remains intact within the eye after removal of the crystalline lens matrix from the natural lens of the eye through an anterior capsule opening in the natural lens. This anterior opening is created by performing an anterior capsulotomy, preferably an anterior capsulorhexis, on the natural lens and is circumferentially surrounded by an anterior capsular rim which is the remnant of the anterior capsule of the natural lens. An improved accommodating intraocular lens according to the invention includes a central optic having normally anterior and posterior sides and extended portions spaced circumferentially about and extending generally radially out from the edge of the optic. These extended portions have inner ends joined to the optic and opposite outer ends movable anteriorly and posteriorly relative to the optic. To this end, the extended portions are either pivotally or flexibly hinged at their inner ends to the optic or are resiliently bendable throughout their length. In this disclosure, the terms "flex", "flexing", "flexible", and the like are used in a broad sense to cover both flexibly hinged and resiliently bendable extended portions. The terms "hinge", "hinged", "hinging", and the like are used in a broad sense to cover both pivotally and flexibly hinged extended portions.

The lens is surgically implanted within the evacuated capsular bag of a patient's eye through the anterior capsule opening in the bag and in a position wherein the lens optic is aligned with the opening, and the outer ends of the lens extended portions are situated within the outer perimeter or cul-de-sac of the bag. The lens has a radial dimension from the outer end of each extended portion to the axis of the lens optic such that when the lens is implanted within the capsular bag, the outer ends of the extended portions engage the inner perimetrical wall of the bag without stretching the bag.

After surgical implantation of the accommodating intraocular lens in the capsular bag of the eye, active endodermal cells on the posterior side of the anterior capsule rim of the bag cause fusion of the rim to the elastic posterior capsule of the bag by fibrosis. This fibrosis occurs about the lens extended portions in such a way that these extended portions are effectively "shrink-wrapped" by the fibrous tissue in such a way as to form radial pockets in the fibrous tissue which contain the extended portions with their outer ends positioned within the outer cul-de-sac of the capsular bag. The lens is thereby fixated within the capsular bag with the lens optic aligned with the anterior capsule opening in the bag. The anterior capsule rim shrinks during fibrosis, and this shrinkage combined with shrink-wrapping of the extended portions causes some radial compression of the lens in a manner which tends to move the lens optic relative to the outer ends of the extended portions in one direction or the other along the axis of the optic. The fibrosed, leather-like anterior capsule rim prevents anterior movement of the optic and urges the optic rearwardly during fibrosis. Accordingly, fibrosis induced movement of the optic occurs posteriorly to a distant vision position in which either or both the optic and the inner ends of the extended portions press rearwardly against the elastic posterior capsule of the capsular bag and stretch this posterior capsule rearwardly.

During surgery, the ciliary muscle of the eye is paralyzed with a ciliary muscle relaxant, i.e. a cycloplegic, to place the muscle in its relaxed state. Following surgery, a ciliary muscle relaxant is periodically introduced into the eye throughout a post-operative fibrosis and healing period (from two to three weeks) to maintain the ciliary muscle in its relaxed state until fibrosis is complete. This drug-induced relaxation of the ciliary muscle prevents contraction of the ciliary muscle and immobilizes the capsular bag during fibrosis. By this means, the lens optic is fixed during fibrosis in its distant vision position within the eye relative to the retina wherein the lens presses rearwardly against and thereby posteriorly stretches the elastic posterior capsule of the capsular bag. If the ciliary muscle was not thus maintained in its relaxed state until the completion of fibrosis, the ciliary muscle would undergo essentially normal brain-induced vision accommodation contraction and relaxation during fibrosis. This ciliary muscle action during fibrosis would result in improper formation of the pockets in the fibrosis tissue which contain the extended portions of the lens. Moreover, ciliary muscle contraction during fibrosis would compress the capsular bag and thereby the lens radially in such a way as to very likely dislocate or decenter the lens from its proper position in the bag or fix the optic in the near vision position.

When the cycloplegic effect of the ciliary muscle relaxant wears off after the completion of fibrosis, the ciliary muscle again becomes free to undergo normal brain-induced contraction and relaxation. Normal brain-induced contraction of the muscle then compresses the lens radially, relaxes the anterior capsule rim, and increases vitreous pressure in the vitreous chamber of the eye. This normal contraction of the ciliary muscle effects anterior accommodation movement of the lens optic for near vision by the combined action of the increased vitreous pressure, anterior capsule rim relaxation, and the anterior bias of the stretched posterior capsule.

Similarly, brain-induced relaxation of the ciliary muscle reduces vitreous pressure, relieves radial compression of the lens, and stretches the anterior capsule rim to effect posterior movement of the lens optic for distant vision.

Normal brain-induced relaxation and contraction of the ciliary muscle after the completion of fibrosis thus causes anterior and posterior accommodation movement of the lens optic between near and distant vision positions relative to the retina. During this accommodation movement of the optic, the lens extended portions undergo endwise movement within their pockets in the fibrous tissue.

The described lens embodiments of the invention conform to one of the following basic lens configurations: (a) a lens configuration, hereafter referred to as a posteriorly biased lens configuration, in which the hinges of hinged extended portions and the inner ends of resiliently bendable extended portions are located posteriorly of or approximately in a plane (tip plane) normal to the optic axis and containing the outer tips of the extended portions when the lens occupies its posterior distant vision position against the posterior capsule of the eye, and (b) a lens configuration, hereafter referred to as an anteriorly biased lens configuration, in which the hinges of hinged extended portions and the inner ends of resiliently bendable extended portions are located forwardly of the tip plane when the lens occupies its posterior distant vision position against the posterior capsule of the eye. Radial compression of a posteriorly biased lens by constriction of the ciliary muscle during accommodation initially urges the lens optic posteriorly against the more dominant anterior forces of the stretched posterior capsule and the increasing vitreous pressure which combine to move the optic forwardly in accommodation against the rearward bias of the compressing lens until the hinges of hinged extended portions or the inner ends of resiliently bendable extended portions move forwardly of the tip plane. Continued radial compression of the lens by ciliary muscle constriction then aids anterior accommodation movement of the lens. Radial compression of an anteriorly biased lens by constriction of the ciliary muscle urges the lens optic anteriorly and thus aids the dominant anterior forces of the stretched posterior capsule and the increasing vitreous pressure throughout the range of lens accommodation.

According to another important aspect of this invention, the extended portions of a presently preferred lens embodiment are generally T-shaped haptics each including a haptic plate and a pair of relatively slender resiliently flexible fixation fingers at the outer end of the haptic plate. In their normal unstressed state, the two fixation fingers at the outer end of each haptic plate extend laterally outward from opposite edges of the respective haptic plate in the plane of the plate and substantially flush with the radially outer end edge of the plate to form the horizontal "crossbar" of the haptic T-shape. The radially outer end edges of the haptic plates are circularly curved about the central axis of the lens optic to substantially equal radii closely approximating the radius of the interior perimeter of the capsular bag when the ciliary muscle of the eye is relaxed. During implantation of the lens in the bag, the inner perimetrical wall of the bag deflects the haptic fingers generally radially inward from their normal unstressed positions to arcuate bent configurations in which the radially outer edges of the fingers and the curved outer end edges of the respective haptic plates conform approximately to a common circular curvature closely approximating the curvature of the inner perimetrical wall of the bag. The outer T-ends of the haptics then press lightly against the perimetrical bag wall and are fixated within the bag perimeter during fibrosis to accurately center the implanted lens in the bag with the lens optic aligned with the anterior capsule opening in the bag.

The haptic plates of certain described lens embodiments are narrower in width than the optic diameter and are tapered so as to narrow in width toward their outer ends. These relatively narrow plates of the haptics flex or pivot relatively easily to aid the accommodating action of the lens and form haptic pockets of maximum length in the fibrous tissue between the haptic fingers and the optic which maximize the accommodation movement of the lens optic. The tapered haptics, being wider adjacent to the optic, can slide radially in the capsular bag pockets during contraction of the of the ciliary muscle to enable forward movement of the optic for vision accommodation.

In some described lens embodiments of the invention, the lens optic and extended portions are molded or otherwise fabricated as an integral one piece lens structure in which the inner ends of the extended portions are integrally joined to the optic, and the extended portions are either resiliently flexible at each point throughout their length or have flexible hinges at their inner ends adjacent the optic at which the extended portions are hingable anteriorly and posteriorly relative to the optic. In other described lens embodiments, the optic and extended portions are formed separately and have mating hinge portions which interengage to pivotally join the optic and extended portions. In some of these described embodiments, the extended portions are T-shaped haptics formed by molding or otherwise forming the flexible haptic fingers integrally with the haptic plates proper. In other described inventive embodiments, the extended portions are T-shaped haptics having T-shaped reinforcing inserts or inlays which both reinforce the haptic plates and provide the haptics with their T-shapes. Still other described embodiments have reinforcing inserts which reinforce the haptics, provide the haptics with their T-shapes, and/or provide the haptics and optic with mating pivotal hinge portions for pivotally connecting the haptics to the optic.

According to another important aspect, the invention provides an accommodating intraocular lens having haptics which are thickened so as to increase in thickness toward their inner ends and have contoured, convexly rounded posterior surfaces adjacent their inner ends. These contoured haptic surfaces and the posterior surface of the lens optic are disposed relative to one another in the axial direction of the optic axis in such a way that when the intraocular lens occupies its posterior distant vision in the eye with the ciliary muscle relaxed, the lens contacts the posterior capsule of the eye in one of the following ways: (a) only the posterior surfaces of the lens haptics contact the posterior capsule, (b) only the posterior surface of the lens optic contacts the posterior capsule, (c) the posterior surfaces of both the haptics and optic contact the posterior capsule. In lens configurations (a) and (c) above, the contoured posterior surfaces of the haptics slide along the posterior capsule during constriction of the ciliary muscle to increase and enhance anterior accommodating movement of the optic. In lens configuration (a), the posterior surface of the optic is spaced from the posterior capsule to permit laser capsulotomy of the posterior capsule without laser damage to the lens optic in the event that the posterior capsule becomes cloudy after implantation of the lens.

A primary and perhaps the most important aspect of the invention is concerned with increasing the accommodation amplitude of the lens, that is the distance the lens optic moves along the axis of the eye during contraction of the ciliary muscle from its relaxed distant vision state to its contracted near vision state. This amplitude is commonly measured and stated in units which are referred to as diopters of accommodation. The maximum accommodation amplitude or diopters of accommodation which the eye will accommodate varies from patient to patient. Some patient's eyes, for example, will accommodate on the order of 3.5 diopters of accommodation. Other patient's eyes will accommodate a maximum of only about 1.75 diopters of accommodation. Accordingly, it is desireable that an accommodating intraocular lens according to this invention be capable of at least 3.5 diopters of accommodation so that it can be used on a patient who can accommodate such a lens and thereby eliminate the need for the patient to wear glasses for near vision.

According to this latter aspect of the invention, the diopters of accommodation of the present accommodating intraocular lens are increased in either or both of the following ways: (a) moving the hinges of lens extended portions or haptics anteriorly relative to the posterior capsule engaging surface(s) of the lens optic in the manner explained earlier so as to increase the portion of ciliary muscle contraction over which the resulting muscular compression of the lens produces an anterior accommodating force on the lens optic, (b) increasing the optical power of the lens, and thereby the amount of vision accommodation produced by any given accommodation movement of the optic, by shaping the optic so that most of its optical power is at the posterior side of the optic and the posterior surface of the optic is steeply curved to retain the optic sharply focused on the retina.

Presently preferred accommodating intraocular lenses of the invention are described. These preferred lenses are anteriorly biased lens including generally T-shaped, flexibly hinged haptics and optics whose posterior portions provide most of the optical power of the optics. These optics cooperate with the anteriorly biased configurations of the lenses to increase accommodation amplitude or diopters of accommodation by both of the ways mentioned above.

BRIEF DESCRIPTION OF THE DRAWINGS

FIG. 1 is an anterior face view of an improved posteriorly biased accommodating intraocular lens according to the invention having hinged extended portions in the form of T-shaped haptics and showing the lens in its normal unstressed state;

FIG. 2 is an edge view of the improved lens in FIG. 1 looking in the direction of the arrow 2 in FIG. 1 and showing the hinging action of the lens haptics in broken lines;

FIG. 4 is an enlarged view taken on line 4—4 in FIG. 3 with portions-broken away for clarity;

FIG. 9 is an anterior face view of a modified accommodating intraocular lens according to the invention having extended portions in the form of resiliently bendable T-shaped haptics;

FIG. 10 is an edge view of the lens in FIG. 9 illustrating the flexibility of the lens haptics;

FIG. 11 is an anterior face view of a modified accommodating intraocular lens according to the invention including three extended portions in the form of hinged T-shaped haptics;

FIG. 12 is an enlarged partial section, similar to the anterior portion of FIG. 3, illustrating a modified posteriorly biased accommodating intraocular lens of the invention having thickened, curved haptics;

FIG. 13 is a fragmentary sectional view similar to a portion of FIG. 12, showing the lens of FIG. 12 after fibrosis of haptic end portions;

FIG. 14 is a view similar to that of FIG. 11 but showing the lens positioned for mid-range vision;

FIG. 15 is a view similar to those of FIGS. 13 and 14 but showing the lens positioned to accommodate near vision;

FIG. 16 is a view similar to FIG. 3 but showing an anteriorly biased accommodating intraocular lens of the invention in its posterior distant vision position within the eye after completion of fibrosis following surgery;

FIG. 17 is an enlargement of the area encircled by the arrow 17—17 in FIG. 16;

FIG. 18 is a further enlarged view of the intraocular lens and natural capsular bag of FIG. 17 showing incoming light rays focused on the retina of the eye;

FIG. 25 is a view similar to FIG. 18 but showing a modified, presently preferred anteriorly biased accommodating intraocular lens according to the invention which provides increased accommodation amplitude and increased diopters of accommodation;

FIG. 26 is an anterior face view of the lens in FIG. 25;

FIG. 27 is an edge view of the lens in FIG. 25; and

FIG. 28 is a view similar to the anterior portion of FIG. 25 showing the preferred intraocular lens in solid lines in a mid-range position of accommodation, in phantom lines in its posterior distant vision position of accommodation, and in dashed lines in its anterior near vision position of accommodation.

DESCRIPTION OF THE PREFERRED EMBODIMENT

Figure 3:
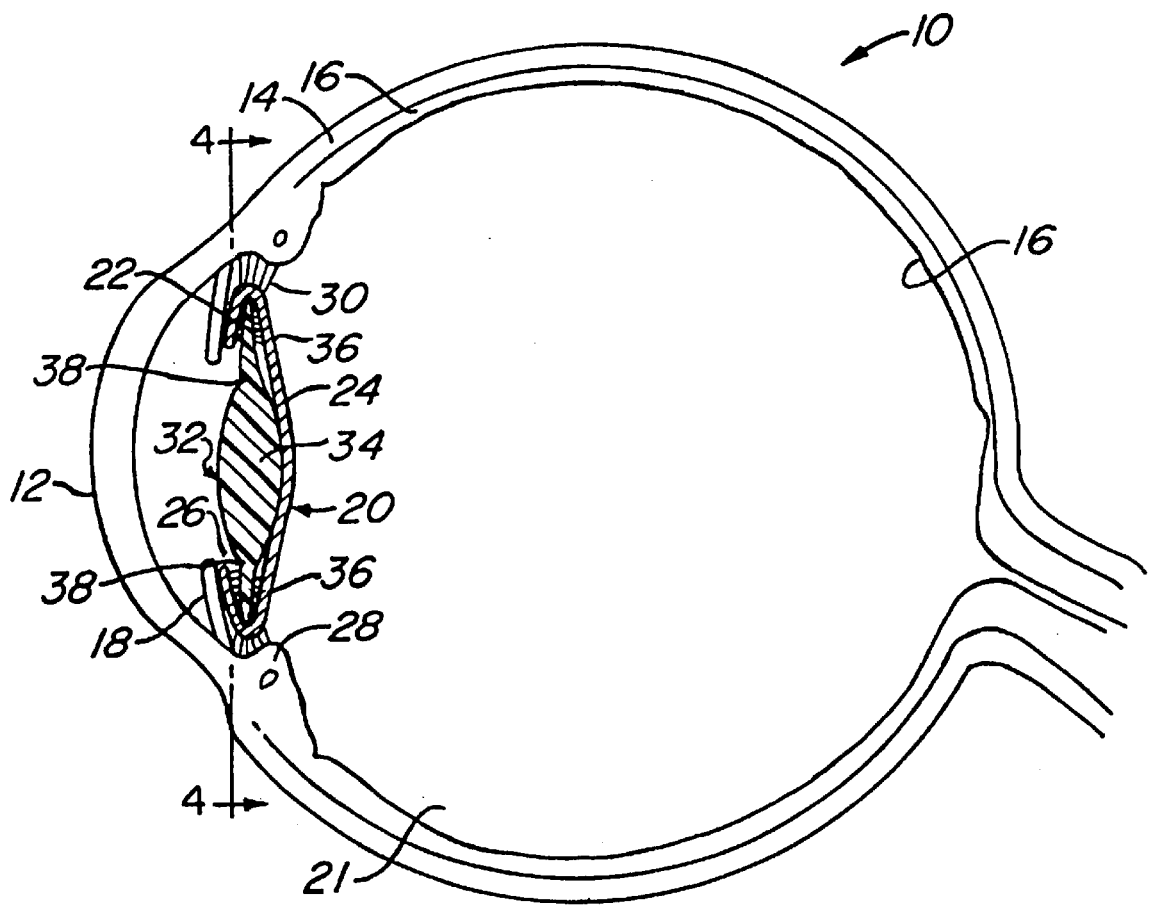
FIG. 3 is a section taken through a human eye having the improved accommodating intraocular lens of FIGS. 1 and 2 implanted within a natural capsular bag in the eye.

Turning now to these drawings, and first to FIG. 3, there is illustrated a human eye 10 whose natural crystalline lens matrix has been removed from the natural lens capsule of the eye through an anterior opening in the capsule formed by an anterior capsulotomy, in this case a continuous tear circular capsulotomy, or capsulorhexis. As noted earlier, this natural lens matrix, which is normally optically clear, often becomes cloudy and forms a cataract which is cured by removing the matrix and replacing it with an artificial intraocular lens.

As mentioned earlier, continuous tear circular capsulotomy, or capsulorhexis, involves tearing the anterior capsule along a generally circular tear line in such a way as to form a relatively smooth-edged circular opening in the center of the anterior capsule The cataract is removed from the natural lens capsule through this opening. After completion of this surgical procedure, the eye includes an optically clear anterior cornea 12, an opaque sclera 14 on the inner side of which is the retina 16 of the eye, an iris 18, a capsular bag 20 behind the iris, and a vitreous cavity 21 behind the capsular bag filled with the gel-like vitreous humor. The capsular bag 20 is the structure of the natural lens of the eye which remains intact within the eye after the continuous tear circular tear capsulorhexis has been performed and the natural lens matrix has been removed from the natural lens.

The capsular bag 20 includes ark annular anterior capsular remnant or rim 22 and an elastic posterior capsule 24 which are joined along the perimeter of the bag to form an annular crevice-like cul-de-sac 25 (FIG. 5) between rim and posterior capsule The capsular rim 22 is the remnant of the anterior capsule of the natural lens which remains after capsulorhexis has been performed on the natural lens. This rim circumferentially surrounds a central, generally round anterior opening 26 (capsulotomy) in the capsular bag through which the natural lens matrix was previously removed from the natural lens. The capsular bag 20 is secured about its perimeter to the ciliary muscle 28 of the eye by zonules 30.

Natural accommodation in a normal human eye having a normal human crystalline lens involves automatic contraction or constriction and relaxation of the ciliary muscle of the eye by the brain in response to looking at objects at different distances. Ciliary muscle relaxation, which is the normal state of the muscle, shapes the human crystalline lens for distant vision. Ciliary muscle contraction shapes the human crystalline lens for near vision. The brain-induced change from distant vision to near vision is referred to as accommodation.

Implanted within the capsular bag 20 of the eye 10 is an accommodating intraocular lens 32 according to this invention which replaces and performs the accommodation function of the removed human crystalline lens. The accommodating intraocular lens may be utilized to replace either a natural lens which is virtually totally defective, such as a cataractous natural lens, or a natural lens that provides satisfactory vision at one distance without the wearing of glasses but provides satisfactory vision at another distance only when glasses are worn. For example, the accommodating intraocular lens of the invention can be utilized to correct refractive errors and restore accommodation for persons in their mid-40s who require reading glasses or bifocals for near vision.

Intraocular lens 32 comprises a unitary body which may be formed of relatively hard material, relatively soft flexible semi-rigid material, or a combination of both hard and soft materials. Examples of relatively hard materials which are suitable for the lens body are methyl methacrylate, polysulfones, and other relatively hard biologically inert optical materials. Examples of suitable relatively soft materials for the lens body are silicone, hydrogels, thermolabile materials, and other flexible semi-rigid biologically inert optical materials.

The lens 32 includes a central optic 34 and T-shaped extended portions or plate haptics 36 extending from diametrically opposite edges of the optic. These haptics include haptic members or plates 36a proper having inner ends joined to the optic and opposite outer free ends and lateral fixation fingers 36b at their outer ends. The haptic plates 36a are longitudinally tapered so as to narrow in width toward their outer ends and may have a width throughout their length less than the diameter of the optic 34, and are resiliently flexible for major portions of their lengths. The haptics 36 are movable anteriorly and posteriorly relative to the optic 34, that is to say the outer ends of the haptics are movable anteriorly and posteriorly relative to the optic. The preferred lens embodiment illustrated is constructed of a resilient semi-rigid material and has flexible hinges 38 which join the inner ends of the haptic plates 36a to the optic. The haptics are relatively rigid and are flexible about the hinges anteriorly and posteriorly relative to the optic as shown in FIG. 2. These hinges are formed by grooves 40 which enter either the anterior or posterior sides and extend across the inner ends of the haptic plates 36a. The haptics 36 are flexible about the hinges 38 in the anterior and posterior directions of the optic. The lens has a relatively flat unstressed configuration, illustrated in FIG. 31 wherein the haptics 36 and their hinges 38 are disposed in a common plane transverse to the optic axis of the optic 34. Deformation of the lens from this normal unstressed configuration by anterior or posterior deflection of the haptics about their hinges creates in the hinges elastic strain energy forces which urge the lens to its normal unstressed configuration. The outer end edges 41 of the haptic plates 36a are preferably circularly curved to equal radii about the optic axis of the optic 34, as shown in FIG. 1. In their normal unstressed state shown in solid lines in FIG. 1, the fingers 36b of each plate haptic 36 extend laterally out from opposite longitudinal edges of the respective haptic plate 36a in the plane of the plate and substantially flush with the outer end edge 41 of the plate. When unstressed, the fingers 36b are preferably bowed with a slight radially inward curvature, as shown in solid lines in FIG. 1. As shown in broken lines in FIG. 1, the fingers 36b are laterally resiliently flexible radially of the haptic plates 36a to their broken line positions of FIG. 1 in which the radially outer edges of the fingers and the end edges 41 of the haptic plates 36a conform substantially to a common circle centered on the axis of the optic 34.

Figure 5:
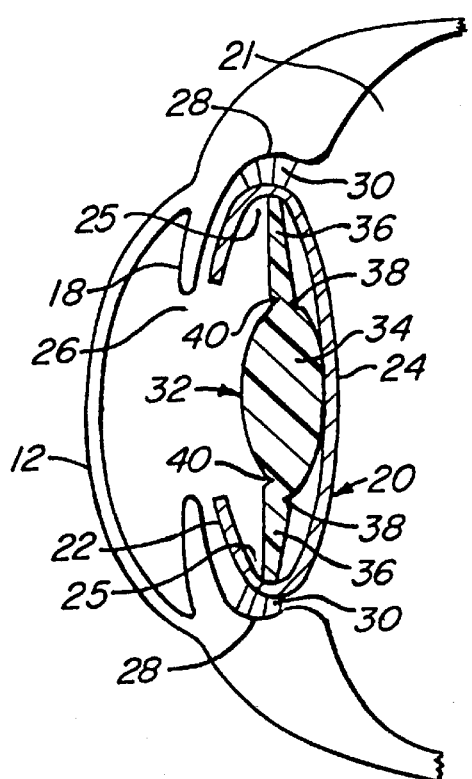
FIG. 5 is an enlarged fragmentary section similar to the anterior portion of FIG. 3 illustrating the initial placement of the lens in the eye.

The accommodating intraocular lens 32 is implanted within the capsular bag 20 of the eye 10 in the position shown in FIGS. 4 and 5. When implanting the lens in the eye, the ciliary muscle 28 of the eye is paralyzed in its relaxed state, shown in FIG. 5, in which this muscle stretches the capsular bag 20 to its maximum diameter. The lens is inserted into the bag through the anterior capsule opening 26 and is sized in length, endwise of the haptics 36, for placement of the lens in the position shown in FIGS. 4 and 5. In this position, the lens optic 34 is aligned with anterior opening 26 in the bag, as shown in FIG. 4. The posterior side of the lens faces the elastic posterior capsule 24 of the capsular bag, and the posterior side of the lens optic 34 is disposed in close proximity to or contacts the posterior capsule. The radially outer T-ends of the lens haptics 36 are positioned within the cul-de-sac 25 of the capsular bag with the outer end edges 41 of the haptic plates 36a and the haptic fingers 36b in close proximity to or seating lightly against the capsular bag cul-de-sac wall. This cul-de-sac wall deflects the haptic fingers inwardly to the positions shown in broken lines in FIG. 4 (which approximate the broken line finger positions shown in FIG. 1). In these deflected positions, the end edges 41 of the haptic plates and the haptic fingers 36b conform closely to the curvature of the cul-de-sac wall to accurately center the lens in the capsular bag. The lens is thus sized and shaped so that when the ciliary muscle 28 is paralyzed in its relaxed state, the lens fits in the capsular bag 20 with a sufficiently close fit to accurately align the lens optic 34 with the anterior capsule opening 26 in the bag without significantly deforming the bag.

The actual dimensions of an intraocular lens according to this invention will be determined by each patient's ocular dimensions. Following are the dimensions of a typical accommodating intraocular lens according to the invention:

| | |
|---|---|
| Diameter of optic 34 | 4.50 mm |
| Inner end width of haptic plates 36a | 1.5 mm |
| Outer end width of haptic plates 36a | 1.3 mm |
| Outer end radius of haptic plates 36a | 5.25 mm |
| Haptic finger thickness | 0.12 mm |
| Distance between unstressed haptic finger tips | 4.5 mm |
| Longitudinal distance between unstressed haptic finger tips | 11.5 mm |

During a post-operative fibrosis and healing period on the order of two to three weeks following surgical implantation of the lens 32 in the capsular bag 20, epithelial cells under the anterior capsular rim 22 of the bag cause fusion of the rim to the posterior capsule 24 by fibrosis. This fibrosis occurs around the lens haptics 36 in such a way that the haptics are "shrink-wrapped" by the capsular bag 20, and the haptics form pockets 42 in the fibrosed material 43. These pockets cooperate with the lens haptics to position and center the lens in the eye. In order to insure proper formation of the haptic pockets 42 and prevent dislocation of the lens by ciliary muscle contraction during fibrosis, sufficient time must be allowed for fibrosis to occur to completion without contraction of the ciliary muscle 28 from its relaxed state of FIG. 5. This is accomplished by introducing a ciliary muscle relaxant (cycloplegic) into the eye before surgery to dilate the pupil and paralyze the ciliary muscle in its relaxed state and having the patient periodically administer cycloplegic drops into the eye during a post-operative period of sufficient duration (two to five weeks) to permit fibrosis to proceed to completion without contraction of the ciliary muscle. The cycloplegic maintains the ciliary muscle 28 in its relaxed state in which the capsular bag 20 is stretched to its maximum diameter (FIG. 5) and immobilized, and the anterior capsular rim 22 is stretched to a taut trampoline-like condition or position. The rim fibroses from this taut condition. The cycloplegic passes through the cornea of the eye into the fluid within the eye and then enters the ciliary muscle from this fluid. While other cycloplegics may be used, atropine is the preferred cycloplegic because of its prolonged paralyzing effect compared to other cycloplegics. One drop of atropine, for example, may last for two weeks. However, to be on the safe side, patients may be advised to place one drop of atropine in the eye every day during the fibrosis period.

The capsular rim 22 shrinks during fibrosis and thereby shrinks the capsular bag 20 slightly in its radial direction. This shrinkage combines with shrink wrapping of the lens haptics 36 produces some opposing endwise compression of the lens which tends to buckle or flex the lens at its hinges 38 and thereby move the lens optic 34 along the axis of the eye. Unless restrained, this flexing of the lens might occur either forwardly or rearwardly. The taut anterior capsular rim 22 pushes rearwardly against and thereby prevents forward flexing of the lens. This fibrosis-induced compression of the lens is not sufficient to interfere with proper formation of the haptic pockets in the fibrosed tissue or cause dislocation of the lens. Accordingly endwise compression of the lens by fibrosis aided by the rearward thrust of the taut capsular rim against the lens haptics 36 causes rearward flexing of the lens from its initial position of FIG. 5 to its position of FIG. 6. The lens haptics 36 are made sufficiently rigid that they will not buckle under the forces of fibrosis. At the conclusion of fibrosis, the lens occupies its posterior position of FIG. 6 wherein the lens presses rearwardly against the elastic posterior capsule 24 and stretches this capsule rearwardly. The posterior capsule then exerts a forward elastic bias force on the lens. This posterior position of the lens is its distant vision position.

Natural accommodation in a normal human eye involves shaping of the natural crystalline lens by automatic contraction and relaxation of the ciliary muscle of the eye by the brain to focus the eye at different distances. Ciliary muscle relaxation shapes the natural lens for distant vision. Ciliary muscle contraction shapes the natural lens for near vision.

Figure 6:
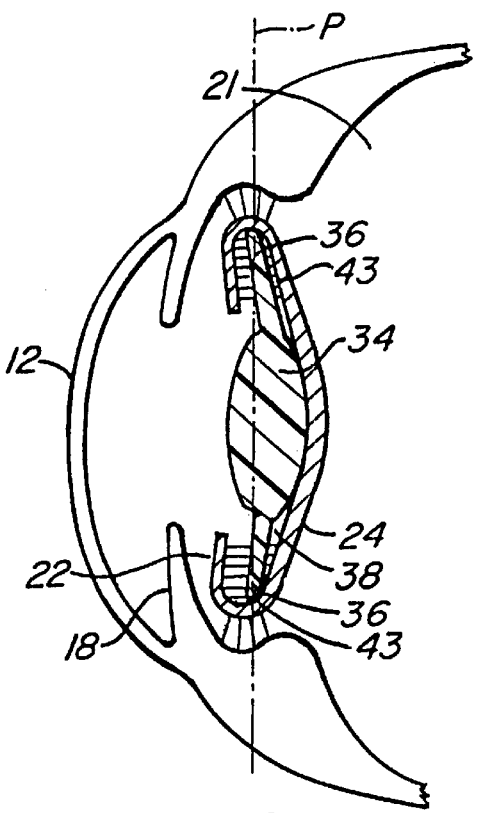
FIGS. 6–8 are sections similar to FIG. 5 illustrating the normal vision-accommodating action of the accommodating lens.
Figure 7:
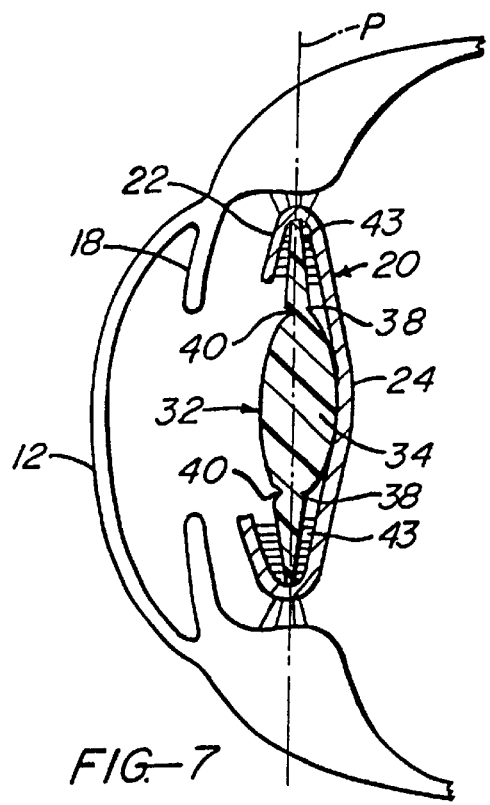
Figure 8:
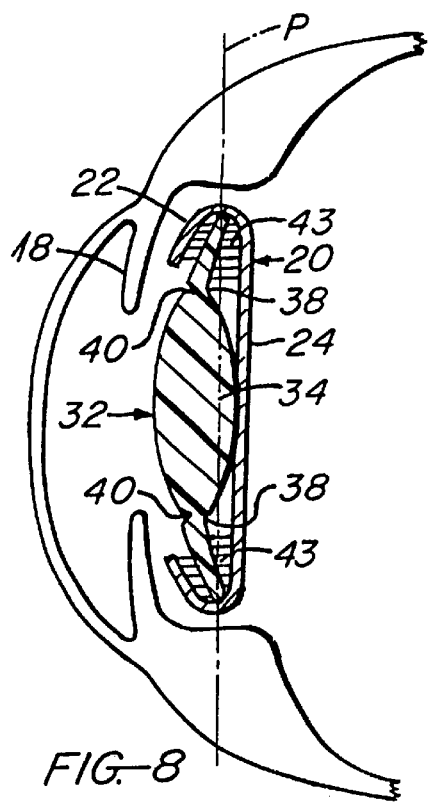

The accommodating intraocular lens 32 is uniquely constructed to utilize this same ciliary muscle action, the fibrosed capsular rim 22, the elastic posterior capsule 24, and the vitreous pressure within the vitreous cavity 21 to effect accommodation movement of the lens optic 34 along the optic axis of the eye between its distant vision position of FIG. 6 to its near vision position of FIG. 8. Thus, when looking at a distant scene, the brain relaxes the ciliary muscles 28. Relaxation of the ciliary muscle stretches the capsular bag 20 to its maximum diameter and its fibrosed anterior rim 22 to the taut condition or position discussed above. The taut rim deflects the lens rearwardly to its posterior distant/vision position of FIG. 8 in which the elastic posterior capsule 24 is stretched rearwardly relative to the general plane of the fibrosed haptic end portions, by the lens and thereby exerts a forward bias force on the lens. When locking at a near scene, such as a book when reading, the brain constricts or contracts the ciliary muscle. This ciliary muscle contraction has the three-fold effect of increasing the vitreous cavity pressure, relaxing the capsular bag 20 and particularly its fibrosed capsular rim 22, and exerting opposing endwise compression forces on the ends of the lens haptics 36 with resultant endwise compression of the lens. Relaxation of the capsular rim permits the rim to flex forwardly and thereby enables the combined forward bias force exerted on the lens by the rearwardly stretched posterior capsule and the increased vitreous cavity pressure to push the lens forwardly relative to the general plane of the fibrosed haptic end portions, in an initial accommodation movement from the position of FIG. 6 to the intermediate accommodation position of FIG. 7.

In this intermediate accommodation position, the lens is substantially flat, and the ends of the lens haptics and their hinges 38 are disposed substantially in a common plane normal to the axis of the eye. Prior to accommodation, the lens arches rearwardly so that endwise compression of the lens by ciliary muscle contraction tends to produce a rearward buckling force on the lens. However, the increased vitreous cavity pressure and the forward bias force of the stretched posterior capsule are sufficient to overcome this opposing rearward buckling force and effect forward accommodation movement of the lens to and at least just slightly beyond the intermediate position of FIG. 7. At this point, endwise compression of the lens by the contracted ciliary muscle produces a forward flexing force on the lens which effects final accommodation of the lens beyond the intermediate position of FIG. 7 to the near vision position of FIG. 8. Subsequent brain-induced relaxation of the ciliary muscle 28 in response to looking at a distant scene reduces the vitreous cavity pressure, stretches the capsular bag 20 to its maximum diameter, and restores the anterior capsular rim 22 to its taut trampoline-like condition to effect return of the lens to its distant viewing position of FIG. 8. During accommodation, the lens optic 34 moves along the axis of the eye. The effective power of the optic is selected by the brain to sharply focus incoming light by moving the optic along the axis of the eye by contraction and relaxation of the ciliary muscle.

The lens haptics 38 flex at their hinges 38 with respect to the lens optic 34 during accommodation. Any elastic strain energy forces developed in the hinges during this flexing produces additional anterior and/or posterior forces on the lens. For example, assume that the lens is relatively flat, i.e., that the lens haptics 36 lie in a common plane as shown in FIG. 1, in the normal unstressed state of the lens. In this case, posterior deflection of the lens from its position of FIG. 1 to its distant vision position of FIG. 6 creates elastic strain energy forces in the hinges 38 which urge the lens forwardly back to its unstressed position of FIG. 1 and thus aid the above discussed initial accommodation of the lens in response to contraction of the ciliary muscle. Final accommodation flexing of the lens from its intermediate position of FIG. 7 to its near vision position of FIG. 8 creates elastic strain energy forces in the hinges 38 which urge the lens rearwardly toward its unstressed position and thus aid initial return of the lens from its near vision position to its distant vision position in response to relaxation of the ciliary muscle. The lens may be designed to assume some other normal unstressed position, of course, in which case any elastic strain energy forces created in the lens during flexing of the haptics will aid, resist, or both aid and resist accommodation of the lens to its near vision position and return of the lens to its distant vision position depending upon the unstressed position of the lens.

During accommodation, the lens haptic plates 36a slide endwise in their fibrosed tissue pockets 42. As shown best in FIGS. 1, 2 and 4, the haptics are tapered endwise in width and thickness to enable the haptics to move freely in the pockets. The lens optic 34 moves forwardly toward and rearwardly away from the anterior capsular rim 22. The diameter of the optic is made as large as possible to maximize its optical imaging efficiency. The optic is preferably but not necessarily made smaller than the diameter of the anterior capsule opening 26 to permit accommodation movement of the optic into and from the opening without interference by the capsular rim 22 in order to maximize the accommodation range.

The modified accommodating intraocular lens 100 shown in FIGS. 9 and 10 is identical to the lens 32 shown in FIGS. 1–8 except as noted below. Thus the modified lens has an optic 102 and generally T-shaped haptics 104 extending radially out from diametrically opposite edges of the optic. These haptics include longitudinally tapered haptic plates 106 and flexible haptic fingers 108 at the outer ends of these plates extending laterally out from the longitudinal edges of the plates. The modified lens 100 differs from the lens 32 only in that the haptic hinges 38 and hinge grooves 40 of the lens 32 are omitted in the modified lens 100, and the haptic plates 108 of the modified lens are made resiliently flexible or bendable throughout their length, as indicated in broken lines in FIG. 10. The modified lens is implanted in a capsular bag of a human eye and provides vision accommodation in response to ciliary muscle contraction and relaxation in the same manner as described in connection with the lens 32.

The accommodating intraocular lens 110 of FIG. 11 differs from the earlier-described lenses, in that it embodies an optic 112 from which extend three haptics 36a extending radially outward. Haptic 36a includes a longitudinally tapered haptic plate 114 and flexible haptic fingers 36b. Although three haptics are shown, it will be understood that four or even more haptics can be provided. Like the lenses earlier described, the lens 110 is implanted in the capsular bag of a patient's eye and provides vision accommodation in response to ciliary muscle contract in and relaxation. The multiple haptics of the lens 110, which can be three or more in number, are equally spaced about the axis of the optic 112 and provide improved centration of the lens in the capsular bag of the eye with the lens optics 112 aligned with the anterior opening in the bag.

The accommodating intraocular lens 200 of FIGS. 12–15 is identical to the lens of FIGS. 1–8 except that the plate portions of the T-shaped extend portions or plate haptics 202 of lens 200 increase in thickness from their outer tip ends toward their inner junctures with the optic 204. The thickened portions of the haptics have convexly curved posterior surfaces 206 which curve rearwardly beyond the posterior surface of the optic 204 and away from the anterior surfaces of the haptics for major portions of the haptic lengths from the outer haptic ends toward the inner haptic ends. The posterior haptic surfaces then curve forwardly toward the anterior haptic surfaces at the inner haptic ends to form thinned flexible hinge portions 208 pivotally joining the haptics to the optic.

The lens 200 is implanted within the capsular bag of a patient's eye in the initial position of FIG. 12, after which fibrosis is permitted to occur about the lens haptics 202 with the ciliary muscle paralyzed in its related state, all in the same manner as explained earlier in connection with FIGS. 1–8. As in FIGS. 1–8, the lens is urged rearwardly toward the posterior capsule 24 of the capsular bag 20 during fibrosis to the posterior distant vision position of FIG. 13. In this posterior position, the rearwardly projecting posterior surfaces 206 of the haptics contact the posterior capsule 24 and space the posterior surface of the optic 204 from the capsule.

Contraction of the ciliary muscle during normal vision accommodation after fibrosis is complete increases vitreous pressure and compresses the lens 200 radially or endwise. The increasing vitreous pressure produced by such muscle contraction together with the rearwardly stretched posterior capsule 24 exert anterior forces, indicated by the arrows V in FIG. 13, on the rearwardly projecting thickened haptics 202. These forces move the lens optic 204 anteriorly for accommodation in much the same manner as explained above in connection with FIGS. 1–8 except for the following haptic movement. During accommodation of lens 200, the arcuate posterior surfaces 206 of the thickened haptics 202 slide inwardly across posterior capsule 24, and the inner ends of the haptics rotate forwardly while their outer ends remain in contact with the posterior capsule, as shown in FIGS. 13–16. This increases the anterior accommodation movement of the optic from its posterior distant vision position of FIG. 13, through its midrange position of FIG. 14, to its near vision position of FIG. 15. When the ciliary muscle relaxes, it radially stretches the capsular bag of the eye and thereby pulls radially out on the encapsulated T-shaped ends of the lens haptics 202 to aid return of the lens to its posterior distant vision position.

Thickening the lens haptics 202 in the manner shown and described provides two advantages in addition to the above mentioned advantage of increasing the accommodation amplitude of the lens optic 204. One of these additional advantages resides in the fact that rearwardly thickening the haptics increases the spacing, along the axis of the optic, between the haptic hinges 208 and the posterior portion of the lens which contacts the posterior capsule 24, in this case the posterior haptic surfaces 206. Increasing this spacing has the effect of shifting the hinges forwardly relative to the posterior capsule 24 and hence forwardly relative to the plane P in FIG. 13 (tip plane) passing through the outer tips of the lens haptics 202 normal to the optic axis when the lens occupies its posterior distant vision position. This forward shift of the hinges relative to the haptic tip plane P, in turn, increases the portion of ciliary muscle contracting during accommodation over which the haptics hinges are located forwardly of the tip plane and hence the portion of such muscle contraction over which compression of the lens 200 by such muscle contraction produces an anterior force on the lens optic which aids vitreous pressure in moving the optic forwardly in accommodation and thereby further increases the accommodation amplitude of the lens.

The second additional advantage of thickening the lens haptics 202 in the manner illustrated (i.e. so that they protrude rearwardly beyond the posterior surface of the lens optic 204) spaces this posterior optic surface from the posterior capsule 24, as shown in FIGS. 13–15. This spacing permits a laser capsulotomy to be performed on the posterior capsule, if it becomes cloudy, by sharply focusing a YAG laser beam on the capsule through the cornea of the eye and the lens optic 204 without the danger of contacting the intense laser beam focus point with the posterior surface of the optic with which would pit or otherwise degrade this optic surface.

It is worthwhile to recall here that accommodating intraocular lenses of the invention conform to one or the other of the following basic lens configurations: (a) a posteriorly biased lens configuration in which the hinges or inner ends of the extended portions or haptics of the lens are located posteriorly of or approximately in a tip plane passing through the outer tips of the extended portions or haptics normal to the optic axis when the lens occupies its posterior distant vision position, (b) an anteriorly biased lens configuration in which the hinges or inner end of the extended portions or haptics are located forwardly of the tip plane when the lens occupies its posterior distant vision position. The accommodating intraocular lenses described to this point are posteriorly biased lenses.

In this regard, it will be seen that the lenses 32, 200 are sized and shaped so that when they assume or occupy their distant vision configurations (i.e. the configurations which the lenses assume or occupy in their posterior distant vision positions of FIGS. 6 and 13), their haptic hinges 38, 208 are located rearwardly of a plane P (tip plane) passing through the outer tips of the lens haptics 36, 202 normal to the optical axis of the lens optics 34, 204. This relationship is attained by sizing and shaping each lens in such a way that the distance or spacing along the optical axis of its optic between the posterior portion(s) of the lens which contact(s) the posterior capsule 24 of the patient's eye (i.e. the posterior surface of the lens optic 34 in FIG. 6 and the posterior surfaces 206 of the thickened lens haptics 202 in FIG. 13) and the lens hinges 38, 208 is less than the distance or spacing along the axis of the eye between the portion(s) of the posterior capsule contacted by the lens and a plane (tip plane P) passing through the annular haptic-tip-receiving sulcus of the capsular bag 20 normal to the axis of the eye.

It is evident from FIGS. 6 and 13 that radial or endwise compression of posteriorly biased lenses 32, 200 by contraction of the ciliary muscle during accommodation initially urges the lens optics 34, 204 rearwardly in opposition to the combined anterior forces of the stretched posterior capsule and the increasing vitreous pressure. These anterior forces are dominant and move the lens optics anteriorly against the opposing posterior bias forces produced by ciliary muscle compression of the lenses to effect vision accommodation, as explained earlier. Initial movement of the haptic hinges 38, 208 during this accommodation occurs forwardly to the mid-range lens positions of FIGS. 7, 14 in which the hinges are located approximately in their tip planes P. Continued compression of the lenses by ciliary muscle contraction at this point moves the hinges forwardly of their tip planes, whereupon the bias forces produced on the lens optics 32, 204 by such lens compression reverse to become anterior forces which aid further anterior accommodation movement of the lenses by vitreous pressure to their near vision positions of FIGS. 8, 12. Relaxation of the ciliary muscle reduces vitreous pressure and stretches the capsular bags radially which pulls the encapsulated T-shaped outer ends of the haptics radially outward to aid return of the lenses to their posterior distant vision positions of FIGS. 6, 13.

Referring now to FIGS. 16–18, there is illustrated an anteriorly biased accommodating intraocular lens 300 according to the invention in its posterior distant vision position within the capsular bag 20 of a patient's eye. Lens 300 is identical to lens 200 except in the following respects. The anterior surfaces 302 of the thickened T-shaped extended portions or plate haptics 304 of lens 300 are flush with the anterior surface of the lens optic 306. The posterior haptic surfaces 308 incline rearwardly away from the anterior haptic surfaces 302 from the outer haptic tips toward their inner junctions with the optic 306 and then forwardly toward the anterior haptic surfaces to define, with the peripheral edge of the optic, posterior V-shaped notches which form thinned flexible hinges 310 at the inner haptic ends. The optic 306 has a convexly rounded posterior surface 312.

Lens 300 is implanted in the capsular bag 20 in the same way as the earlier described lenses and is subjected to the same ciliary muscle contraction and relaxation as the earlier described lenses during normal vision accommodation following completion of fibrosis. Lens 300 is so sized and shaped that the posterior surfaces 308 of its haptics 304 and the posterior surface 312 of its optic 306 contact the posterior capsule 24 of the bag 20. When the lens 300 occupies its posterior distant vision configuration of FIGS. 16–18 which it assumes in its posterior distant vision position shown in the latter figures, its hinges 310 are located a small distance forwardly of the haptic tip plane P of the lens, i.e. a plane passing through the outer tips of the haptics 304 and the annular haptic-tip-receiving sulcus of the capsular bag 20 normal to the axis of the lens and the eye. Accordingly, during ciliary muscle contraction in the course of normal accommodation, end to end or radial compression of the lens 300 and vitreous pressure both exert anterior accommodation forces on the lens optic 306 throughout its full accommodation range. This combined action of the two forces increases the accommodation amplitude and hence diopters of accommodation of the lens.

Figures 19, 20, 21:
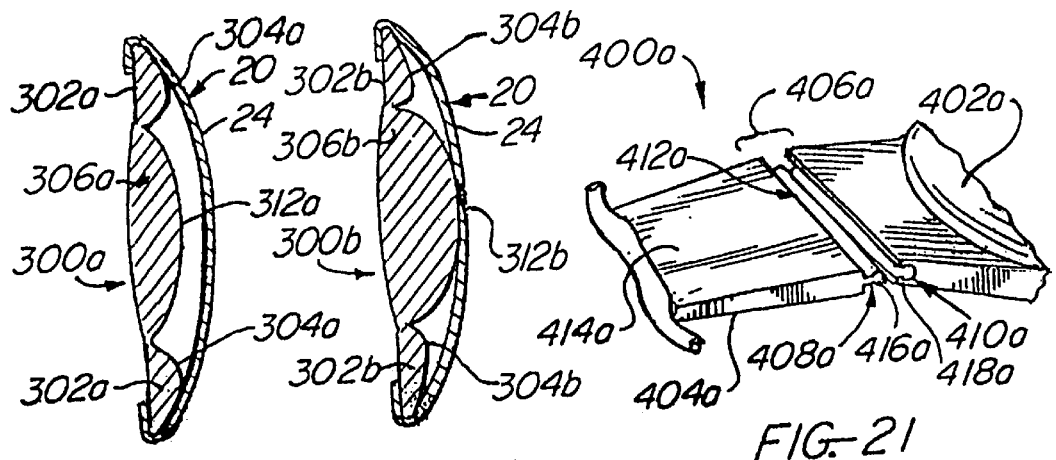
FIGS. 19 and 20 are views similar to the anterior portion of FIG. 18 but illustrating two modified anteriorly biased accommodating intraocular lenses according to the invention in their posterior distant vision positions within the capsular bag of the eye.
FIG. 21 in an exploded fragmentary perspective view of a modified accommodating intraocular lens according to the invention having pivotally hinged haptics.

FIGS. 19 and 20 illustrates two modified anterior biased accommodating intraocular lenses 300a and 300b according to the invention implanted within a capsular bag 20 of a patient's eye. These modified anterior biased lenses are identical to and undergo accommodation in much the same manner as the anterior biased lens of FIGS. 16–18 with the following exceptions. In lens 300a, only the posterior surfaces 304a of the T-shaped extended portions or plate haptics 302a of the lens contact the posterior capsule 24 of the capsular bag. Accordingly, vitreous pressure acts only on these haptics during accommodation, and the lens optic is immune to laser damage during laser capsulotomy of the posterior capsule, as in the lens 200 of FIGS. 12–15. The posterior surface 312a of the lens optic 306a is spaced from the posterior capsule. In lens 300b, only the posterior surface 312b of the lens optic 306b contacts the posterior capsule 24 of the capsular bag. The posterior surfaces 304b of the T-shaped plate haptics 302b of the lens are spaced from the posterior capsule. Accordingly, during accommodation, vitreous pressure acts only on the posterior surface of the optic.

Figures 22, 23:
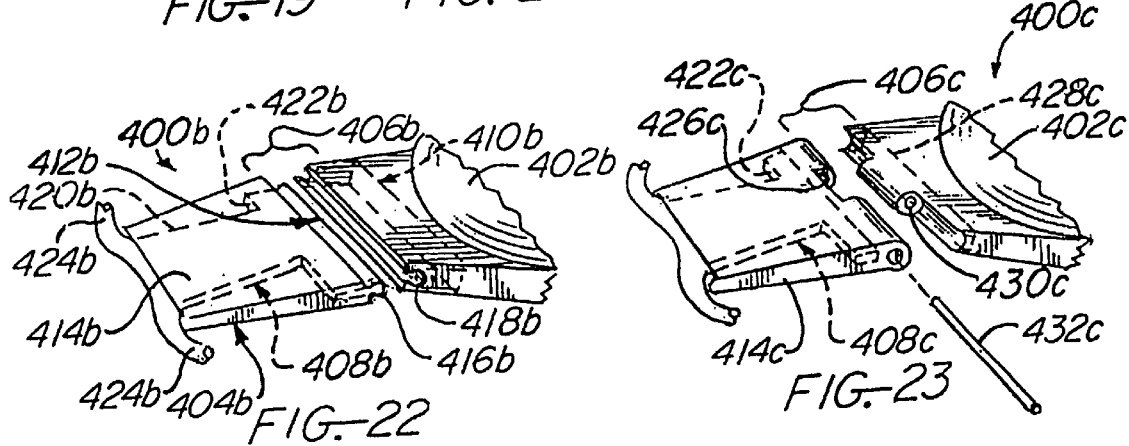
FIG. 22 is a view similar to FIG. 21 but showing a modified haptic hinge arrangement including reinforcing hinge inserts or inlays.
FIG. 23 is a view similar to FIG. 22 showing a modified hinge arrangement.

All of the accommodating intraocular lenses of the invention described to this point, except the lens of FIGS. 9 and 10, have hinged extended portions in the form of haptics with resiliently flexible haptic hinges. FIGS. 21–23 illustrate modified lenses having extended portions in the form of pivotally hinged haptics. The lens 400a of FIG. 21 includes a central optic 402a and T-shaped plate haptics 404a (only one shown) spaced circumferentially about and joined by pivotal hinges 406a to the edge of the optic. Each haptic hinge 406a comprises mating hinge portions 408a, 410a on the respective haptic and the optic which pivotally interengage to pivotally connect the haptics to the optic for anterior and posterior movement of the haptics relative to the optic. In FIG. 21, each haptic hinge portion 408a comprises a tongue 412a integrally molded or otherwise formed along the inner end of and coplanar with the respective haptic plate portion 414a and having a generally cylindrical head 416 along the inner edge of the tongue. Each optic hinge portion 410a includes a hinge groove or channel 418a along the edge of the optic 402a which opens laterally outward toward the haptic. Each hinge groove 418a is cylidrically curved, undercut and sized in transverse cross-section to pivotally receive the bead 416a on the adjacent haptic tongue 412a in such a way that the head is captivated in the groove, and the respective haptic 404a is pivotally movable through a certain angle anteriorly and posteriorly relative to the optic.

The optic 402a and each haptic plate 414a may be molded or otherwise fabricated from any suitable intraocular lens material including the intraocular lens materials listed earlier. All of these materials have suitable optical and other qualities for an intraocular lens. Some of these materials are sufficiently hard or firm to permit each haptic hinge tongue 412a to be molded or otherwise formed integrally with its haptic plate 414a and each haptic hinge groove 418a to be molded or otherwise formed directly in the material of the lens optic 402a, as in the lens 400a of FIG. 21.

The modified accommodating intraocular lenses 400b of FIG. 22 and 400c of FIG. 23 are essentially identical to less 400a of FIG. 21 except in the following respects. The optics and haptic plates of lenses 400b, 400c are made from a material which is not sufficiently firm or hard to use for hinge purposes, and their hinge formations are separately fabricated from intraocular lens materials which are suitably hard or firm for hinge purposes and which form reinforcing hinge inserts or inlays that are molded within the optics and the haptic plates of the lenses 400b, 400c. For this reason, the parts of lenses 400b, 400c are designated by the same reference numerals as their corresponding parts of lens 400a but with the subscripts b or c, as the case may be.

With the foregoing in mind, each extended portion or haptic 404b of lens 400b comprises an elongate hinge plate 420b which is encapsulated within, extends edgewise through, and forms a reinforcing insert or inlay within the respective haptic plate 414b. At the inner end of this hinge plate is a cross-bar 422b which projects edgewise beyond the inner end of the haptic plate 414b to form the tongue 412b of the respective haptic hinge position 408b. At the outer end of each hinge plate 420b are flexible fingers 424b which provide the lens haptic 404b with its T-shape. Each optic hinge portion 410b comprises a bar which is encapsulated within and forms a reinforcing insert or inlay in the edge of the lens optic 402b. Along the outer edge of this bar is the hinge groove or channel 418b which pivotally receives the cylindrical bead 416b along the adjacent hinge tongue 412b.

The modified lens 400c of FIG. 23 is identical to lens 400b except that the inner end of each haptic plate 414c of lens 400c extends endwise beyond the inner cross bar 422c of the reinforcing hinge plate 408b which forms the respective haptic hinge portion 408c of lens 400c. This extending inner end of each haptic plate 414c has a cylindrically rounded surface and a central slot 426c. Each optic hinge portion 410c comprises a hinge bar 428c encapsulated in the edge of the lens optic 402c and having a central rounded hinge projection 420c. This hinge projection fits rotatably within the notch 426c of the adjacent haptic hinge portion 408c and is pivotally connected to the haptic hinge portion, to form the respective haptic hinge 406c, by a hinge pin 432c which extends through aligned bores in the haptic hinge portion and the optic hinge projection.

Figure 24:
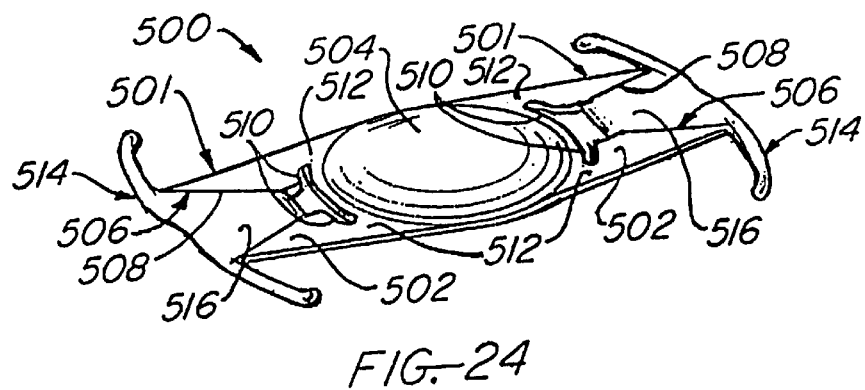
FIG. 24 is a perspective view of a further modified accommodating intraocular lens according to the invention having hinged extended portions in the form of reinforced plate haptics.

The modified accommodating intraocular lens 500 of FIG. 24 has extended portions in the form of flexibility hinged plate haptics 501 including flexible haptic plate portions 502 integral with and extending radially out from edges of the lens optic 504, the plate haptics being generally resiliently flexible throughout at least a major portion of their lengths. These haptic plate portions have cutouts 506 including tapered longitudinal outer ends 508 which widen toward and open through the outer ends of the haptics and arcuate inner end slots 510 which extend laterally toward the longitudinal edges of the haptics to form flexible haptic hinges 512 between the outer ends of the slots and the longitudinal edges of the haptic portions. Haptics 501 are reinforced longitudinally outward of the hinges 512 by T-shaped inserts 514 having tapered inner end portions 516 fixed within the tapered outer ends 508 of the haptic cutouts 506. Lens 500 is implanted in the eye in the same manner as the earlier described lens and flexes at its flexible hinges 512 during contraction and relaxation of the ciliary muscle to effect vision accommodation.

FIGS. 25–28 illustrate a presently preferred accommodating intraocular lens 600 according to the invention implanted within a capsular bag 20 of a patient's eye. This preferred lens is an anteriorly biased lens with flexibly hinged extended portions in the form of T-shaped haptics which achieves increased accommodation amplitude and increased droplets of accommodation by the combined action of (a) its anteriorly biassed configuration which increases accommodation amplitude and increased diopters of accommodation in the manner explained earlier, and (b) increased power of its optic which increases the amount of accommodation produced by any given amount of accommodation movement of the lens optic or, conversely reduces the accommodation movement of the optic required to produce any given amount of accommodation.

Lens 600 comprises a one piece lens structure having a central optic 602 and flexibly hinged extended portions 604 in the form of T-shaped plate haptics extending generally radially out from the optic. Each plate haptic 604 is longitudinally tapered in width and thickness so as to widen in width and increase in thickness toward its inner end. Each plate haptic includes an inner plate portion 606 which is integrally joined to an edge of the optic 602 and inclines anteriorly relative to the optic toward its outer end, an outer plate portion 608 joined to the outer end of the inner plate portion, and a V-groove 610 entering the posterior side of the haptic at the juncture of these plate portions so as to form at this juncture a flexible hinge 612. The outer plate portion 608 is pivotally movable at this hinge anteriorly and posteriorly relative to the inner plate portion 606 and the optic 602. The lens structure including its optic 602 and haptic plate portions 606, 608 is molded or otherwise formed as a unitary lens structure from a lens material mentioned earlier and has T-shaped inserts 614 fixed in the outer ends of the outer haptic plate portions 608. These inserts provide the lens extended portions or haptics 604 with their T-shape and may be utilized to reinforce the outer haptic plate portions 608 if necessary.

Lens 600 is implanted in the capsular bag 20 of the eye with the ciliary muscle of the eye paralyzed in its relaxed state and maintained in this paralyzed state until the completion of fibrosis, all in the same manner as explained earlier. During this fibrosis, the lens optic 602 is urged posteriorly to its distant vision position shown in solid lines in FIG. 25 and dashed lines in FIG. 28 wherein the posterior surface of the optic presses rearwardly against the posterior capsule 24 of the capsular bag and stretches this posterior capsule rearwardly. The configuration which the lens 600 assumes or occupies in this posterior distant vision position is its posterior distant vision configuration. Ciliary muscle contraction during normal vision accommodation following completion of fibrosis increases vitreous pressure and compresses the lens radially or endwise to effect anterior accommodation movement of the lens optic 602 in the same manner as explained earlier.

As mentioned above, lens 600 is an anteriorly biased lens. In this regard, it will be observed in FIGS. 25 and 28 that when the lens occupies its posterior distant vision position, its haptic hinges 612 are located forwardly of a tip plane $P_T$ passing through the outer tips of the lens haptics 604 normal to the axis of the lens optic 602 and the eye. Accordingly, compression of the lens by ciliary muscle contraction during normal vision accommodation is effective to produce an anterior accommodation force on the optic throughout its entire accommodation range from its posterior distant vision through its mid-range position (solid lines in FIG. 28) to its anterior near vision position (phantom lines in FIG. 28). Compression of the lens by ciliary muscle contraction thereby aids the anterior vitreous pressure force on the optic throughout its entire accommodation range and thereby increases the accommodate amplitude and diopters of accommodation of the lenses, as explained earlier.

An important feature of lens 600 resides in the fact that its optic 602 has increased optical or dioptic power which aids the anterior biased configuration of the lens to further increase accommodation amplitude and diopters of accommodation. To this end, the anterior face 616 of the optics is relatively flat or just slightly convex while the posterior face 618 of the optic has a relatively steep convex curvature such that the optic has a generally planoconvex shape. This optic shape locates most or all of the optical power of the optic at the posterior side of the optic. Increasing the power of the lens optic in this way decreases the distance through which the optic must move to produce any given amount of vision accommodation and, conversely, increases the amount of vision accommodation produced by any given accommodation movement of the optic and thereby increases the maximum accommodation amplitude and diopters of accommodation of the lens.

Increasing the power of an intraocular lens optic at the posterior side of the optic, as in FIGS. 25–28, shifts the optical plane of the optic (i.e. plane from which the focal point of the optic originates) rearwardly toward the retina 16 of the eye. For example, the optical plane $P_O$ of lens optic 602 is located at the approximate position shown in FIG. 25 which is rearwardly of the optical plane position (not shown) of a symmetrical biconvex optic of the same center thickness measured along the axis of the optic but having anterior and posterior surfaces of equal curvature). This rearward shaft of the optical plane of the optic toward the retina must be compensated for by increasing the dioptic power of the optic in order to sharply focus incoming light rays on the retina. The required increase in the power of optic 602 is accomplished by appropriately shaping the steep convex curvature of the posterior surface 618 of the optic.

At this point, refer again to FIGS. 16–20 in which it will be observed that the lens illustrated in each of these figures includes a central optic whose posterior surface has a greater convex curvature than its anterior surface. Accordingly, the lens optic illustrated in each of the FIGS. 16–20 is a "rear power" optic most of whose optical power is provided by the posterior surface of the optic. Accordingly, the lenses of FIGS. 16–20 provide increased accommodation amplitude and diopters of accommodation in essentially the same manner as explained above in connection with FIGS. 25–28.

The inventor claims:

1. An accommodating intraocular lens for implantation into a generally circular inner surface of an eye, comprising:
    (a) an optic;
    (b) at least two haptics spaced apart from each other and extending generally radially away from the optic, adapted to engage the generally circular inner surface of the eye for holding the lens in the eye;
    (c) each of the haptics including an outer portion with a surface adapted to engage the generally circular inner surface of the eye, at least part of said outer surface extending beyond the diameter of the generally circular inner surface of the eye, when said outer portions is in its unstressed state, said outer portion being flexible and not conforming to the generally circular inner surface of the eye until subjected to compressive forces, so that the outer surface will conform generally to the shape of the inner surface of the eye when subjected to said compression forces upon implantation; and
    (d) the haptics being flexible along at least a portion of their respective lengths to move the optic anteriorly and/or posteriorly in response to forces imparted to the lens through contraction and expansion of the generally circular inner surface of the eye.

2. The lens of claim 1, wherein the optic is circular.

3. The lens of claim 1, wherein the haptics are connected to and extend from an outer edge of the optic.

4. The lens of claim 1, wherein the lens is formed of a single piece of material.

5. The lens of claim 1, wherein two haptics extend from opposite sides of the optic.

6. The lens of claim 1, wherein three haptics are spaced apart an equal distance from each other around the optic.

7. The lens of claim 1, wherein the haptics include opposed longitudinal edges that taper inwardly as they extend from the optic.

8. The lens of claim 1, wherein the haptics include upper and lower surface that taper inwardly as they extend from the optic.

9. The lens of claim 1, wherein the haptics include a lower surface extending rearwardly beyond a horizontal plane of a posterior surface of the optic.

10. The lens of claim 1, wherein at least a portion of a haptic upper surface extends forwardly beyond a horizontal plane of a anterior surface of the optic.

11. The lens of claim 1, wherein the haptics and optic are positioned in a normally uniplanar alignment when unstressed.

12. The lens of claim 1, wherein each haptic includes an outer end and said outer portion includes a pair of fingers extending from the outer end.

13. The lens of claim 12, wherein the fingers are relatively straight in their unstressed state.

14. The lens of claim 12, wherein the fingers are curved inwardly in their unstressed state.

15. The lens of claim 12, wherein the fingers are formed integrally with each haptic.

16. The lens of claim 12, wherein the fingers are attached to the outer end of each haptic.

17. The lens of claim 12, wherein the fingers extend from opposite sides of each haptic.

18. The lens of claim 12, wherein the fingers include an enlarged portion adapted to be encapsulated by the inner surface of the eye so as to hold the haptics in place relative to the inner surface of the eye when the inner surface of the eye expands and contracts.

19. The lens of claim 18, wherein the enlarged portion is a knob.

20. The lens of claim 1, wherein each haptic includes at least one hinge adapted to allow the optic to move posteriorly when the inner surface of the eye expands and to move anteriorly when the inner surface contracts.

21. The lens of claim 20, wherein the hinge has an elastic memory operable to bias the hinge back to its normally unstressed position following contraction or expansion of the inner surface of the eye.

22. The lens of claim 21, wherein the hinge is a groove extending across at least one side of the haptic.

23. An accommodating intraocular lens for implantation into a generally circular inner surface of an eye, comprising:
   (a) an optic;
   (b) at least two haptics spaced apart from each other and extending generally radially away from the optic, adapted to engage the generally circular inner surface of the eye for holding the lens in the eye;
   (c) each of the haptics including an other portion with a surface shaped to engage the generally circular inner surface of the eye, at least part of said outer surface extending beyond the diameter of the generally circular inner surface of the eye, when said outer portion is in its unstressed state, said outer portion being flexible and not conforming to the generally circular inner surface of the eye until subjected to compressive forces, so that the outer surface will conform generally to the shape of the inner surface of the eye when subjected to said compression forces upon implantation; and
   (d) each of the haptics include including at least one hinge adapted to move the optic anteriorly and/or posteriorly in response to forces imparted to the lens through contraction and expansion of the generally circular inner surface of the eye.

24. The lens of claim 23, wherein the hinge has an elastic memory operable to bias the hinge back to its normally unstressed position following contraction or expansion of the inner surface of the eye.

25. The lens of claim 23, wherein the hinge is a groove extending across at least one side of the haptic.

26. The lens of claim 23, wherein at least a portion of each haptic is rigid.

27. The lens of claim 23, wherein the optic is circular.

28. The lens of claim 23, wherein the haptics are connected to and extend from an outer edge of the optic.

29. The lens of claim 23, wherein the lens is formed of a single piece of material.

30. The lens of claim 23, wherein two haptics extend from opposite sides of the optic.

31. The lens of claim 23, wherein three haptics are spaced apart an equal distance from each other around the optic.

32. The lens of claim 23, wherein the haptics include opposed longitudinal edges that taper inwardly as they extend from the optic.

33. The lens of claim 23, wherein the haptics include upper and lower surface that taper inwardly as they extend from the optic.

34. The lens of claim 23, wherein the haptics include a lower surface that is convexly curved.

35. The lens of claim 34, wherein the haptics lower surface extends rearwardly beyond a posterior surface of the optic.

36. The lens of claim 23, wherein each haptic includes an outer end and said outer portion includes a pair of fingers that extend from the outer end.

37. The lens of claim 36, wherein the fingers are relatively straight in their unstressed state.

38. The lens of claim 36, wherein the fingers are curved inwardly in their unstressed state.

39. The lens of claim 36, wherein the fingers are formed integrally with each haptic.

40. The lens of claim 36, wherein the fingers are attached to the outer end of each haptic.

41. The lens of claim 36, wherein the fingers extend from the outer end of each haptic.

42. The lens of claim 36, wherein the fingers extend from opposite sides of each haptic.

43. The lens of claim 36, wherein the fingers include an enlarged portion adapted to be encapsulated by the inner surface of the eye so as to hold the haptics in place relative to the inner surface of the eye when the inner surface of the eye expands and contracts.

44. The lens of claim 43, wherein the enlarged portion is a knob.

45. An accommodating intraocular lens for implantation into a generally circular inner surface of an eye, comprising:
   (a) an optic;
   (b) at least two haptics spaced apart from each other and extending generally radially away from the optic, adapted to engage the generally circular inner surface of the eye for holding the lens in the eye;
   (c) each of the haptics including an outer portion with a surface adapted to engage the generally circular inner surface of the eye, at least part of said outer surface extending beyond the diameter of the generally circular inner surface of the eye, when said outer portion is in its unstressed state, said outer portion being flexible and not conforming to the generally circular inner surface of the eye until subjected to compressive forces, so that the outer surface will conform generally to the shape of the inner surface of the eye when subjected to said compression forces upon implantation, said outer portion shaped to be encapsulated by the inner surface of the eye so as to hold the haptics in place relative to the inner surface of the eye when the inner surface of the eye expands and contracts; and
   (d) the haptics being flexible along at least a portion of their respective lengths to move the optic anteriorly and/or posteriorly in response to forces imparted to the lens through contraction and expansion of the generally circular inner surface of the eye.

46. The lens of claim 45, wherein said outer portion is T-shaped, the T-shaped outer portion having two free ends.

47. The lens of claim 46, wherein the free ends include enlarged portions.

48. The lens of claim 46, wherein at least one of the free ends is knob shaped.

49. The lens of claim 46, wherein at least one of the free ends of disc shaped.

50. The lens of claim 45, wherein each haptic includes at least one hinge adapted to allow the optic to move posteriorly when the inner surface of the eye expands and to move anteriorly when the inner surface contracts.

51. The lens of claim 50, wherein said at least one of the hinges is a reduced portion of the haptic.

52. The lens of claim 50, wherein the hinge has an elastic memory operable to bias the hinge back to its normally unstressed position following contractions or expansion of the inner surface of the eye.

* * * * *